(12) United States Patent
Chien

(10) Patent No.: US 10,016,388 B2
(45) Date of Patent: Jul. 10, 2018

(54) OPHTHALMIC LENS, INTRAOCULAR LENS, AND OPHTHALMIC LENS PACKAGE HAVING OPHTHALMIC LENS

(71) Applicant: HON HAI PRECISION INDUSTRY CO., LTD., New Taipei (TW)

(72) Inventor: Hsiu-Wen Chien, New Taipei (TW)

(73) Assignee: HON HAI PRECISION INDUSTRY CO., LTD., New Taipei (TW)

( * ) Notice: Subject to any disclaimer, the term of this patent is extended or adjusted under 35 U.S.C. 154(b) by 2 days.

(21) Appl. No.: 15/268,700

(22) Filed: Sep. 19, 2016

(65) Prior Publication Data

US 2018/0055814 A1 Mar. 1, 2018

(30) Foreign Application Priority Data

Aug. 26, 2016 (TW) .............................. 105127486 A

(51) Int. Cl.
*A61K 31/352* (2006.01)
*A61K 9/00* (2006.01)
*A61L 12/12* (2006.01)
*G02B 1/04* (2006.01)

(52) U.S. Cl.
CPC .......... *A61K 31/352* (2013.01); *A61K 9/0051* (2013.01); *A61L 12/12* (2013.01); *G02B 1/043* (2013.01)

(58) Field of Classification Search
CPC .............................. A61K 9/0051; G02B 1/043
See application file for complete search history.

(56) References Cited

U.S. PATENT DOCUMENTS

| 2013/0172419 A1* | 7/2013 | Saxena | .................. C08G 77/38 |
|---|---|---|---|
| | | | 514/570 |
| 2013/0303627 A1* | 11/2013 | Miyano | .................... A61K 9/06 |
| | | | 514/675 |

FOREIGN PATENT DOCUMENTS

WO WO-2005077176 A1 * 8/2005 ............. A61K 31/70

OTHER PUBLICATIONS

Gulsen et al., "Ophthalmic drug delivery through contact lenses", IOVS, Jul. 2004, vol. 45, No. 7, pp. 2342-2347.*

* cited by examiner

*Primary Examiner* — Gina C Justice
(74) *Attorney, Agent, or Firm* — ScienBiziP, P.C.

(57) ABSTRACT

An ophthalmic lens or an intraocular lens releasing anthocyanin for the benefit of a user's eyes includes a matrix and anthocyanin dispersed in the matrix. An ophthalmic lens package includes a lens protection solution and the ophthalmic lens, the ophthalmic lens is immersed in the lens protection solution.

2 Claims, No Drawings

OPHTHALMIC LENS, INTRAOCULAR LENS, AND OPHTHALMIC LENS PACKAGE HAVING OPHTHALMIC LENS

This application claims the benefit of priority under 35 USC 119 from Taiwan Patent Application 105127486, filed on Aug. 26, 2016.

FIELD

The subject matter herein generally relates to an ophthalmic lens, an intraocular lens, and an ophthalmic lens package having the ophthalmic lens.

BACKGROUND

Ophthalmic lens and intraocular lens are both popular. The ophthalmic lenses and the intraocular lens are not immune to bacteria invasions however.

DETAILED DESCRIPTION

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. Also, the description is not to be considered as limiting the scope of the embodiments described herein. The drawings are not necessarily to scale and the proportions of certain parts may be exaggerated to better illustrate details and features of the present disclosure.

The term "comprising," when utilized, means "including, but not necessarily limited to"; it specifically indicates open-ended inclusion or membership in the so-described combination, group, series, and the like.

An ophthalmic lens releasing anthocyanin includes a matrix and anthocyanin dispersed in the matrix is described.

An intraocular lens releasing anthocyanin includes a matrix and anthocyanin dispersed in the matrix is described.

An ophthalmic lens package that includes a lens protection solution and an ophthalmic lens releasing anthocyanin immersed in the lens protection solution and is described. The ophthalmic lens includes a matrix and anthocyanin dispersed in the matrix.

According to a first embodiment of an opthalmic lens is disclosed. The opthalmic lens is configured for slowly releasing anthocyanin, as the opthalmic lens includes a matrix and anthocyanin dispersed in the matrix. The ophthalmic lens can be contact lens, such as a hydrogel lens or a silicone hydrogel lens.

Anthocyanin is one type of flavonoids and is found in natural vegetables, fruit, and other plants. Anthocyanin is an anti-oxidant, is antiviral and can diminish inflammation. Anthocyanin protects eyes from harmful bacteria and provides nutrients for eyes.

In at least one embodiment, the anthocyanin can be extracted from red onions, kidney beans, pomegranates, or grapes.

In at least one embodiment, the anthocyanin has a mass percentage of about 0.005% to about 3% of a total mass of the ophthalmic lens.

In at least one embodiment, when the ophthalmic lens is a hydrogel lens, the matrix is hydrogel. When the ophthalmic lens is a silicone hydrogel lens, the matrix is silicone hydrogel.

In detail, when the matrix is hydrogel, the matrix is formed by an ultraviolet (UV) photopolymerization reaction of a hydrogel pre-polymer. The hydrogel pre-polymer includes at least one hydrophilic monomer, at least one photoinitiator, and at least one crosslinker. The anthocyanin can be mixed into the hydrogel pre-polymer before the UV photopolymerization reaction. After the UV photopolymerization reaction, the anthocyanin forms in the gaps between molecules of the matrix.

The hydrophilic monomer includes, but is not limited to, at least one acrylic-based monomer (CR'H=CRCOX), where R is H or $CH_3$, R' is H, $CH_3$ or alkali, X is O, N, or one of the hydrophilic groups. Preferably, the hydrophilic monomer is 2-hydroxyethyl methacrylate (HEMA), N-, N-dimethylacrylamide acrylamide (DMA), methacrylic acid (MAA), N-Vinylpyrrolidone (NVP), polyethylene glycol methacrylate (PEGMA), sulfobetaine methacrylate (SBMA), or a combination thereof. The hydrophilic monomer has a mass percentage of about 40% to about 90% of the total mass of the hydrogel pre-polymer.

The crosslinker is ethylene glycol dimethacrylate (EGDMA), trimethylolpropane trimethacrylate (TMPTMA), N,N'-Methylenebisacrylamide (MBAA), or a combination thereof. The crosslinker has a mass percentage of about 0.1% to about 5% of the total mass of the hydrogel pre-polymer.

The photoinitiator is available commercially from Chemical Industries Basel (CIBA) Corporation as a clear liquid under the trade name "Irgacure-1173". The photoinitiator has a mass percentage of about 0.15% to about 5% of the total mass of the hydrogel pre-polymer.

The hydrogel pre-polymer may further include a solvent as water, ethanol, hexanol or a combination thereof. The solvent has a mass percentage of about 10% to about 49% of the total mass of the hydrogel pre-polymer.

When the matrix is silicone hydrogel, the matrix is formed by an ultraviolet (UV) photopolymerization reaction of a silicone hydrogel pre-polymer. The silicone hydrogel pre-polymer includes at least one hydrophilic monomer, at least one silicone monomer, at least one photoinitiator, and at least one crosslinker. The anthocyanin can be mixed into the silicone hydrogel pre-polymer before the UV photopolymerization reaction. After the UV photopolymerization reaction, the anthocyanin forms in the gaps between molecules of the matrix.

The hydrophilic monomer includes, but is not limited to, at least one acrylic-based monomer (CR'H=CRCOX), wherein R is H or $CH_3$, R' is H, $CH_3$ or alkali, X is O, N, or one of the hydrophilic groups. Preferably, the hydrophilic monomer is 2-hydroxyethyl methacrylate (HEMA), N-, N-dimethylacrylamide acrylamide (DMA), methacrylic acid (MAA), N-Vinylpyrrolidone (NVP), polyethylene glycol methacrylate (PEGMA), sulfobetaine methacrylate (SBMA), or a combination thereof.

The silicone monomer includes, but is not limited to, silicone-containing (—Si—O—Si—) monomer, macromere, or a mixture thereof. Preferably, the silicone monomer includes Tris(hydroxymethyl)aminomethane (Tris), Polydimethylsiloxane (PDMS), or a combination thereof.

The hydrophilic monomer and the silicone monomer have a combined mass percentage of about 40% to about 90% of the total mass of the silicone hydrogel pre-polymer.

The crosslinker is ethylene glycol dimethacrylate (EGDMA), trimethylolpropane trimethacrylate (TMPTMA), N,N'-Methylenebisacrylamide (MBAA), or a combination thereof. The crosslinker has a mass percentage of about 0.1% to about 5% of the total mass of the silicone hydrogel pre-polymer.

The photoinitiator may be Irgacure 1173. The photoinitiator has a mass percentage of about 0.15% to about 5% of the total mass of the silicone hydrogel pre-polymer.

The silicone hydrogel pre-polymer may further include a solvent as water, ethanol, hexanol or a combination thereof. The solvent has a mass percentage of about 10% to about 49% of the total mass of the silicone hydrogel pre-polymer.

An intraocular lens, according to a second embodiment, is configured for slowly releasing anthocyanin. The second embodiment includes the matrix and the anthocyanin dispersed in the matrix.

An ophthalmic lens package having the ophthalmic lens includes lens box and a lens protection solution, wherein the ophthalmic lens is immersed in the lens protection solution.

The lens protection solution may include anthocyanin, and preferably, the anthocyanin has a mass percentage of about 0.005% to about 5% of a total mass of the lens protection solution.

The main constituents of the lens protection solution are water and sodium chloride (NaCl). The lens protection solution further may include salts and agents, such as potassium chloride (KCl), disodium hydrogen phosphate ($Na_2HPO_4$), potassium dihydrogen phosphate ($KH_2PO_4$), sodium borate ($Na_2B_4O_7$), boric acid ($H_3BO_3$), or a combination thereof, for maintaining osmotic pressure and antibacterial

EXAMPLE 1

A method for manufacturing the ophthalmic lens includes providing and mixing HEMA, I1173, EGDMA, ethanol and anthocyanin, to obtain a mixture. The mixture is cross-linked and cured by a UV-light curing process (ultraviolet light at a wavelength of about 365 nanometers), to form a hydrogel lens. The ophthalmic lens is obtained by swelling the hydrogel lens.

The HEMA has a mass percentage of 79.425% of the total mass of the mixture. The Irgacure 1173 has a mass percentage of 0.845% of the total mass of the mixture. The EGDMA has a mass percentage of 0.83% of the total mass of the mixture. The anthocyanin has a mass percentage of 0.9% of the total mass of the mixture. The ethanol has a mass percentage of 18% of the total mass of the mixture.

The anthocyanin has a mass percentage of 1.08% of a total mass of the ophthalmic lens.

EXAMPLE 2

A method for manufacturing the ophthalmic lens includes providing and mixing HEMA, DMA, TRIS, PDMS, I1173, EGDMA, hexanol and anthocyanin, to obtain a mixture. The mixture is cross-linked and cured by a UV-light curing process to form a silicone hydrogel lens. The ophthalmic lens is obtained by swelling the silicone hydrogel lens.

The HEMA has a mass percentage of 6.97% of the total mass of the mixture. The DMA has a mass percentage of 23.6% of the total mass of the mixture. The TRIS has a mass percentage of 45.5% of the total mass of the mixture. The PDMS has a mass percentage of 0.3% of the total mass of the mixture. The Irgacure 1173 has a mass percentage of 1.03% of the total mass of the mixture. The EGDMA has a mass percentage of 0.95% of the total mass of the mixture. The anthocyanin has a mass percentage of 0.5% of the total mass of the mixture. The ethanol has a mass percentage of 21.15% of the total mass of the mixture.

The anthocyanin has a mass percentage of 0.64% of a total mass of the ophthalmic lens.

EXAMPLE 3

The lens protection solution includes water, NaCl, and anthocyanin. The anthocyanin has a mass percentage of 0.03% of a total mass of the lens protection solution. The NaCl has a mass percentage of 0.9% of a total mass of the lens protection solution.

EXAMPLE 4

The lens protection solution includes water, NaCl, anthocyanin, KCl, $Na_2HPO_4$, and $KH_2PO_4$. The anthocyanin has a mass percentage of 0.05% of a total mass of the lens protection solution. The NaCl has a mass percentage of 0.8% of a total mass of the lens protection solution. The KCl has a mass percentage of 0.02% of a total mass of the lens protection solution. The $Na_2HPO_4$ has a mass percentage of 0.142% of a total mass of the lens protection solution. The $KH_2PO_4$ has a mass percentage of 0.027% of a total mass of the lens protection solution.

EXAMPLE 5

The lens protection solution includes water, NaCl, anthocyanin, $H_3BO_3$, and $Na_2B_4O_7$. The anthocyanin has a mass percentage of 0.08% of a total mass of the lens protection solution. The NaCl has a mass percentage of 0.65% of a total mass of the lens protection solution. The $H_3BO_3$ has a mass percentage of 0.5% of a total mass of the lens protection solution. The $Na_2B_4O_7$ has a mass percentage of 0.04% of a total mass of the lens protection solution.

EXAMPLE 6

The ophthalmic lens of example 1 or example 2 is immersed into the lens protection solution of example 1, example 2, or example 3. The ophthalmic lens and the lens protection solution are packaged into the lens box and disperse disinfectant to form the ophthalmic lens package.

It is to be understood, even though information and advantages of the present embodiments have been set forth in the foregoing description, together with details of the structures and functions of the present embodiments, the disclosure is illustrative only; changes may be made in detail, especially in matters of shape, size, and arrangement of parts within the principles of the present embodiments to the full extent indicated by the plain meaning of the terms in which the appended claims are expressed.

What is claimed is:
1. An intraocular lens releasing anthocyanin, comprising:
a matrix; and
anthocyanin dispersed in the matrix;
wherein the anthocyanin has a mass percentage of about 0.005% to about 3% of a total mass of the intraocular lens.

2. The intraocular lens of claim 1, wherein the matrix is hydrogel or silicone hydrogel.

* * * * *